US00PP26011P2

(12) United States Plant Patent
Sal

(10) Patent No.: US PP26,011 P2
(45) Date of Patent: Oct. 20, 2015

(54) *HOSTA* PLANT NAMED 'DIAMONDS ARE FOREVER'

(50) Latin Name: ***Hosta* hybrid (Tratt.)**
Varietal Denomination: Diamonds Are Forever

(71) Applicant: Eric M. Sal, Hamilton, MI (US)

(72) Inventor: Eric M. Sal, Hamilton, MI (US)

(73) Assignee: Walters Gardens, Inc., Zeeland, MI (US)

( * ) Notice: Subject to any disclaimer, the term of this patent is extended or adjusted under 35 U.S.C. 154(b) by 278 days.

(21) Appl. No.: 13/986,081

(22) Filed: Mar. 29, 2013

(51) Int. Cl.
*A01H 5/12* (2006.01)

(52) U.S. Cl.
USPC ..... Plt./353

(58) Field of Classification Search
USPC ..... Plt./353
CPC ..... A01H 5/0272; A01H 5/02; A01H 5/12; A01H 5/00
See application file for complete search history.

(56) References Cited

PUBLICATIONS

Walters Gardens, Inc. Wholesale Catalog Summer 2012-Spring 2013, 5 pages total.*
Walters Gardens, Inc. Descriptive New Item List—Summer 2012 through Spring 2013, pp. 1 and 13.*

* cited by examiner

*Primary Examiner* — June Hwu

(57) ABSTRACT

The new and distinct *Hosta* plant named 'Diamonds Are Forever' with small, compact, mound habit, small elliptic to cordate leaves with dark green centers and wide creamy white margins that develop into a white. Numerous purple striped flowers are held attractively above foliage in mid-summer.

2 Drawing Sheets

Botanical classification: *Hosta* hybrid (Tratt.).
Variety denomination: 'Diamonds Are Forever'.

BACKGROUND OF THE INVENTION

The present invention relates to the new and distinct *Hosta* plant, *Hosta* 'Diamonds Are Forever' discovered by Eric M. Sal at a nursery in Zeeland, Mich., USA in the summer of 2009 as an uninduced whole plant mutation in a tissue cultured crop of *Hosta* 'Diamond Tiara' (not patented). The new plant has been successfully asexually propagated both by division and by tissue culture at the same nursery in Zeeland, Mich. and in both asexual propagation systems found to be stable and produce identical plants that maintain the unique characteristics of the original plant.

BRIEF SUMMARY OF THE INVENTION

*Hosta* 'Diamonds Are Forever' differs from its parent, 'Diamond Tiara', as well as all other *Hostas* known to the applicant. There are over 5,000 *Hosta* cultivars registered with the American *Hosta* Society, which is the registrar for the genus *Hosta*. There is a similar number of about 5,000 unregistered cultivars. *Hosta* 'Diamonds Are Forever' is a mutation from *Hosta* 'Diamonds Tiara'. *Hosta* 'Diamond Tiara' is a mutation from *Hosta* 'Golden Tiara' along with many other sports and mutations from the Tiara Group including: 'Amber Tiara' (not patented), 'Crystal Tiara' (not patented), 'Emerald Scepter' (not patented), 'Emerald Tiara' (not patented), 'Gilded Tiara' (not patented), 'Grand Prize' (not patented), 'Grand Tiara' (not patented), 'Heavenly Tiara' (not patented), 'Ivory Tiara' (not patented), 'Lime Tiara' (not patented), 'Margaret Mary Tiara' (not patented), 'Opal Tiara' (not patented), 'Pearl Tiara' (not patented), 'Platinum Tiara' (not patented), 'Ribbon Tiara' (not patented) and 'Topaz Tiara' (not patented).

All of the above have similar flower color and similar leaf shape with varying variegation, leaf colorations or other minor changes. The most similar cultivars with green leaf centers and white margins are: 'Diamond Tiara', 'Ivory Tiara', 'Margaret Mary Tiara', 'Pearl Tiara' and 'Ribbon Tiara'. 'Diamond Tiara', 'Margaret Mary Tiara' and 'Pearl Tiara' all have thinner white margins than 'Diamonds Are Forever', and 'Margaret Mary Tiara' also has a more sinuate leaf margin compared to the flat margin of the new plant. 'Ribbon Tiara' has more yellow in the margin and much slower growing than the new plant. *Hosta* 'Ivory Tiara' is similar in having a wide white margin and leaves of thicker substance, but it is a mutation stemming from 'Grand Tiara' and not 'Diamond Tiara' as in the case of the new plant. 'Diamonds Are Forever' seems to have variegation with an intermediate color between the margin and the center that has more whitish-green segments than 'Ivory Tiara'. 'Diamonds Are Forever' has a leaf thickness measured between the veins of fully expanded leaves of 0.0105" compared to 'Golden Tiara' and 'Diamond Tiara' which have been measured at 0.0065" to 0.0070".

*Hosta* 'Diamonds Are Forever' differs from all these registered and unregistered cultivars known to the inventor in the following combined traits:

1. Plant of small, compact, mound habit with upright to gradually arching foliage.
2. Small elliptic to cordate leaves with dark green centers and wide creamy white margins that develop into a white.

3. Numerous purple striped flowers held attractively above foliage in mid-summer.

BRIEF DESCRIPTION OF THE DRAWINGS

The photographs of the three-year old plant demonstrate the overall appearance of the near-mature plant, including the unique traits, grown in a partially-shaded trial garden in Zeeland, Mich. with supplemental water and fertilizer as needed. The colors are as accurate as reasonably possible with color reproductions. Ambient light spectrum, source, direction and temperature may cause the appearance of minor variation in color.

DETAILED BOTANICAL DESCRIPTION

Figure 1:
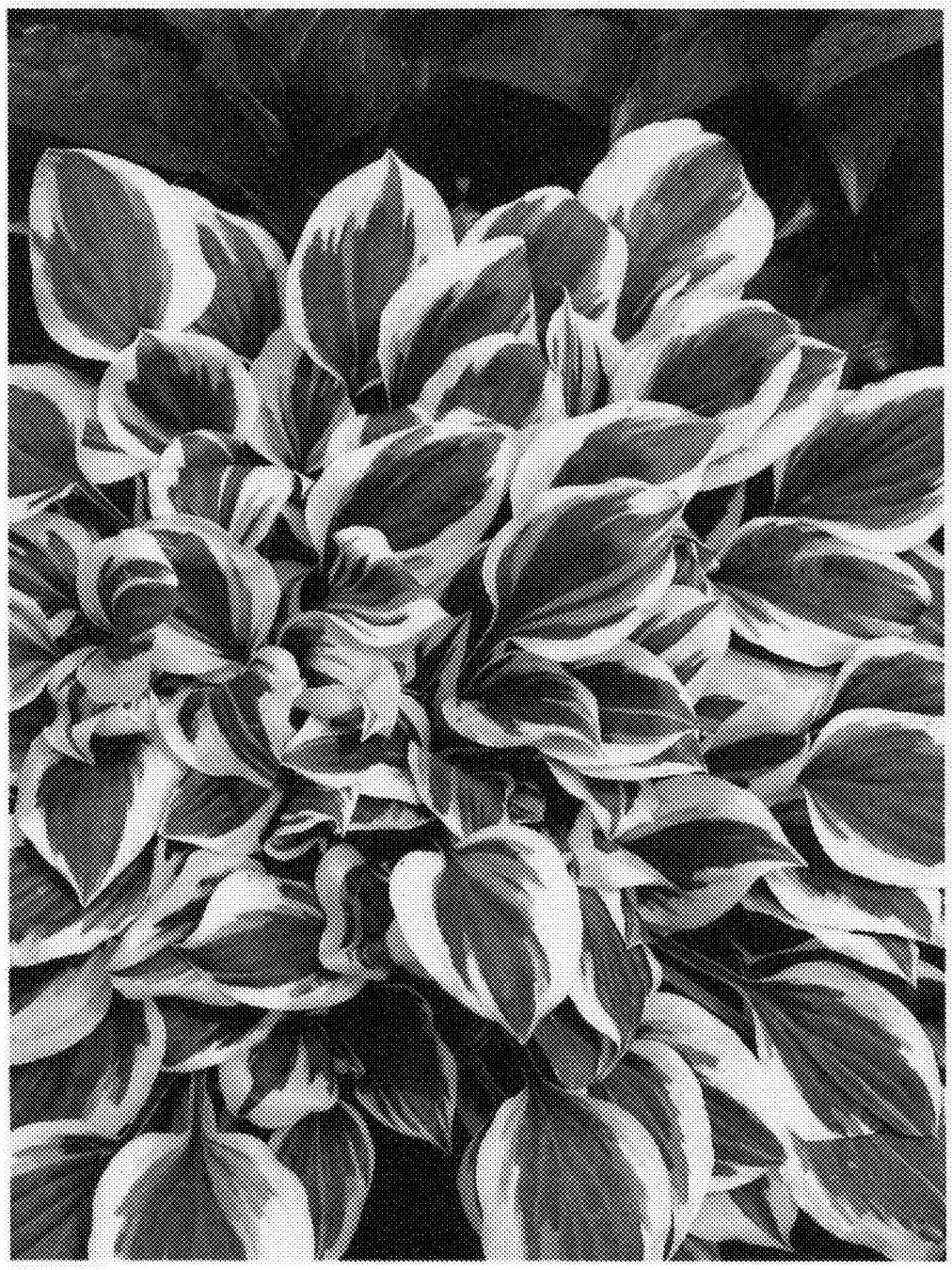
FIG. 1 shows a whole plant in the early part of the growing season prior to flowering.
Figure 2:
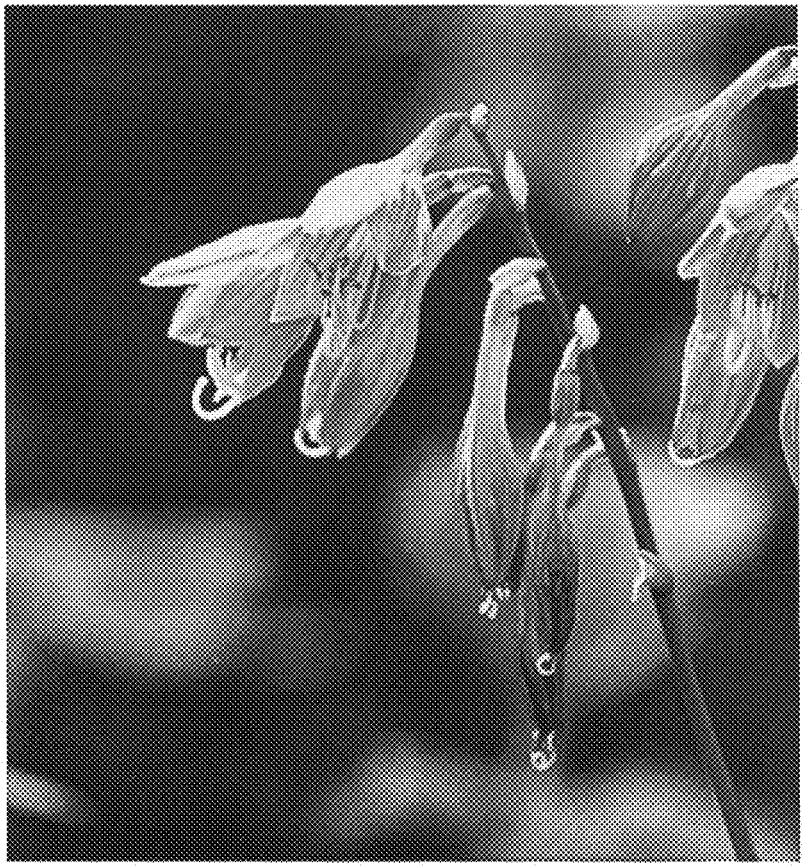
FIG. 2 shows a close-up of the flowers.

The following descriptions and color references are based on the 2001 edition of The Royal Horticultural Society Colour Chart except where common dictionary terms are used. The new plant, *Hosta* 'Diamonds Are Forever', has not been observed under all possible environments. The phenotype may vary slightly with different environmental conditions, such as temperature, light, fertility, moisture and specimen maturity, but without any change in the genotype. The following observations and size descriptions are of a three-year old plant in a trial garden in Zeeland, Mich. with 50% artificial shade, supplemental water and light fertilizer as needed.

Botanical classification: *Hosta* hybrid.

Parentage: Whole plant mutation of *Hosta* 'Diamond Tiara' (not patented).

Propagation method: By sterile laboratory tissue culture propagation and garden division.

Growth rate: Moderate to rapid.

Crop time: Summer growing 9 to 10 weeks to finish in a one-liter container.

Time to initiate roots from tissue culture about sixteen to eighteen days.

Plant description:

*Plant shape and habit*.—Hardy, long-lived, herbaceous perennial, densely rhizomatous, forming a radially symmetrical mounded clump in maturity, with basal rosette of leaves.

*Roots*.—Normal, fleshy, lightly branching, cream-colored in normal soil.

*Plant size*.—Foliage height about 22.0 cm tall; width of plant at the widest point is approximately 45 cm at the widest point just above soil line.

Foliage description:

*Leaf blade*.—Cordate, entire margins, cordate leaf base with acute apex, flat, mostly bilaterally symmetrical, without sinuous or pie-crust margins, with only slightly impressed veins; blade width to length ratio of about 1:1.25; average about 8.0 cm wide and 10.0 cm long; glabrous; adaxial surface glaucous, dull matte-finished late in growing season, abaxial surface (bottom) slightly vitreous remaining throughout growing season; margin variegation portion increasing with age from ⅓ to nearly ½ total leaf width.

*Blade color*.—Early season as emerging adaxial center between RHS 139A and RHS 139B, adaxial margin nearest RHS 158A, intermediate colors of RHS 145C, nearest RHS N138D and nearest RHS 148D in both long and small irregular patches between the margin and center; early season as emerging abaxial center nearest RHS N138B, abaxial margin between RHS 11C and RHS 11D, intermediate colors of between RHS 144A and RHS 144B. Mid-season and later adaxial center between RHS 139A and darker than RHS 137A, margin white, lighter than RHS 155D and large and small irregular intermediate patches of whiter or lighter than RHS N138D, nearest RHS 144A, and more green than RHS 191D and lighter than RHS 147D; mid-season and later abaxial center nearest RHS 138A, margins lighter or more white than RHS 155D and small irregular intermediate patches of nearest RHS 145D and lighter than RHS 147D.

*Veins*.—6 to 7 pairs of major parallel veins on either side of one main center vein increasing with years of maturity; nearly flat only slightly impressed.

*Vein color*.—Generally on early season and mid-season abaxial and adaxial surfaces the same color as surrounding leaf blade tissue in margin, center and intermediate patches.

*Petioles*.—Concavo-convex, glabrous, glaucous, upright to arching; 10 to 12 cm long and about 0.6 cm wide measured at 2 cm above soil line.

*Petiole color*.—Adaxial and abaxial margins in early season and mid to late season the same colors as blade leaf margins for that period; adaxial center nearest RHS 144A and abaxial center nearest RHS 139B.

Flower description:

*Buds*.—Clavate, with acute apex and long thin base; one day prior to opening about 6.0 cm long, and 1.5 cm wide at the broadest portion and 4.0 mm wide at fused tube.

*Bud color*.—Nearest RHS 85D on fused tube portion with veins of RHS 85C, veins darkening to nearest RHS 86B on distal end with stripes of lighter than RHS 85D; 2.0 mm green apex nearest RHS 138B.

*Flowers*.—12 to 20 per scape; each subtended by bract; funnelform; opening to about 3.2 cm wide and 6.5 cm long, (distal flowers slightly smaller); remain open for a normal period, usually one to two days on or cut from plant; persist dried on scape; scapes remain effective from early-July into late-July in Zeeland, Mich.; no detectable fragrance.

*Tepals*.—Two sets of three fused at the basal two thirds; acute apex; margins entire; glabrous, approximately 6.5 cm long and 1.5 cm wide.

*Tepal color*.—Abaxial inner and outer tepal sets color nearest RHS N88D with three darker veins of nearest RHS N88B extending proximally toward base of nearest RHS 85D; inner tepal set with clear transparent margin of about 1.0 to 1.5 mm; adaxial inner and outer tepal sets center middle portion nearest RHS 86C with three veins of nearest RHS 86A; proximal adaxial color nearest RHS 85D.

*Pedicel*.—Rounded, glaucous, glabrous; about 9.0 mm long, 3.0 mm diameter; nearly horizontal, curved slightly downward with age.

*Pedicel color*.—Between RHS 138D and RHS 139D.

*Peduncle*.—Cylindrical, glaucous, glabrous, unbranched; usually one per division; nearly vertical with little or no arching; about 4 mm diameter at base, about 40 cm tall.

*Peduncle color*.—Nearest RHS 139B.

*Gynoecium*.—Single. Style: about 6.5 cm long, 1.5 mm diameter, curved upward at distal 1.5 cm; lighter (more white) than RHS 11D the whole length. Stigma: rounded, 1 mm to 2 mm in diameter; color nearest RHS 155D. Ovary: oval, about 6 mm long and 3 mm diameter; color between RHS 145A and RHS 145B.

*Androecium*.—Six. Filaments: six, about 1.0 mm in diameter and 5.5 cm long, shorter than gynoecium; slightly curve upward the proximal 1.0 mm; lighter than RHS 11D throughout. Anthers: oblong; dorsifixed, versatile, dehiscing longitudinal; about 3 mm long and 1 mm wide, color between RHS N187B and RHS 187A. Pollen: elliptical, less than 0.1 mm long, nearest RHS 13B.

*Bracts*.—Subtending each flower with one or two below flowers, ovate to lanceolate, entire, glaucous, glabrous, concavo-convex, widest at middle and tapering to acute apex, sessile, clasping about ½ peduncle; protruding upward, about 60 degree angle from vertical at time of flower opening; lowest bracts before flowers adpressed against peduncle, about 1.5 mm long and 5.0 mm across; bracts subtending flowers beginning proximally about 1.2 cm long and 6.0 mm across decreasing distally; remaining green after flowers drop.

*Bract color*.—Abaxial and adaxial center between RHS N138B and RHS 139B; abaxial and adaxial margins 1.0 to 2.0 mm wide nearest RHS 155D.

Fruit: Tri-valved capsule; about 2.2 cm long and 5.5 mm diameter; acute apex and rounded base; color as maturing between RHS 138A and RHS 139B; dried color between RHS 161A and RHS 161B.

Seeds: Flattened single-winged nutlet with amplified embryo at one end; about 5.0 mm long, about 2.0 mm wide and about 1.0 mm thick at embryo; about 18 seeds per capsule; color nearest RHS 202A.

Disease and pest resistance: Disease or pest resistance beyond that common to *Hostas* has not been observed. The new plant grows best with light fertilizer, plenty of moisture and adequate drainage, but is able to tolerate some flooding and drought when mature. Hardiness at least from USDA zone 3 through 9.

I claim:

1. A new and distinct ornamental *Hosta* plant named 'Diamonds Are Forever' as herein described and illustrated suitable as a potted plant, for landscaping the garden en masse or as an accent, and for cut flower or leaf arrangements.

* * * * *